United States Patent [19]

Ohnota et al.

[11] Patent Number: 5,308,856

[45] Date of Patent: May 3, 1994

[54] THIAZOLIDINE-2,4-DIONE DERIVATIVES, SALTS AND PREPARATION PROCESSES THEREOF

[75] Inventors: Michiro Ohnota, Nogi; Kyuya Okamura; Yoshihiro Hirata, both of Ohmiya; Koji Murakami, Nogi; Mitsuo Ohashi, Ohmiya, all of Japan

[73] Assignee: Kyorin Pharmaceutical Co., Ltd., Tokyo, Japan

[21] Appl. No.: 938,228

[22] PCT Filed: Feb. 24, 1992

[86] PCT No.: PCT/JP92/00190

§ 371 Date: Oct. 26, 1992

§ 102(e) Date: Oct. 26, 1992

[87] PCT Pub. No.: WO92/14730

PCT Pub. Date: Sep. 3, 1992

[30] Foreign Application Priority Data

Feb. 25, 1991 [JP] Japan .................................. 3-53278

[51] Int. Cl.$^5$ ................. C07D 417/10; A61K 31/435
[52] U.S. Cl. ..................................... 514/369; 548/181
[58] Field of Search ......................... 548/181; 514/369

[56] References Cited

FOREIGN PATENT DOCUMENTS 57-28073  2/1982  Japan .
57-48983  3/1982  Japan .
1-19077   1/1989  Japan .

Primary Examiner—Robert Gerstl
Attorney, Agent, or Firm—Oblon, Spivak, McClelland, Maier & Neustadt

[57] ABSTRACT

The present invention provides novel thiazolidine-2,4-dione derivatives possessing blood sugar-lowering action and aldose reductase-inhibitory action, their salts, their preparation processes and drugs containing them, and relates to thiazolidine-2,4-dione derivatives represented by a general formula (1)

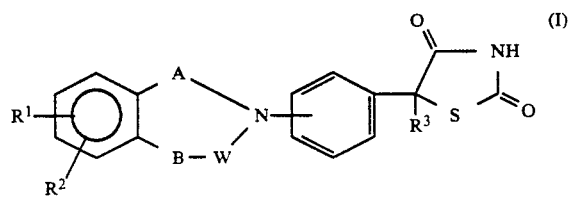

[wherein $R^1$ and $R^2$ denote identically or differently hydrogen atoms, halogens, lower alkyl groups, hydroxyl groups, lower alkoxy groups, nitro groups or amino groups (said amino group may be substituted with lower alkyl group or lower alkanoyl group, $R^3$ denotes a hydrogen atom or lower alkyl group, A denotes a lower alkylene or carbonyl group, and B and W denote differently lower alkylenes, carbonyl groups or bonding hands], or their salts.

3 Claims, No Drawings

THIAZOLIDINE-2,4-DIONE DERIVATIVES, SALTS AND PREPARATION PROCESSES THEREOF

TECHNICAL FIELD

The present invention relates to novel thiazolidine-2,4-dione derivatives possessing blood sugar-lowering action and aldose reductase-inhibitory action, their salts, their preparation processes and a drug containing them.

BACKGROUND TECHNIQUES

As therapeutic agents for diabetes, various biguanide type and sulfonylurea type compounds have been used so far. However, the biguanide type compounds cause the lactic acid acidosis and the sulfonylurea type compounds cause serious hypoglycemia posing a problem on their adverse effect, thus the advent of therapeutic agent for diabetes without such defect is desired.

On the other hand, it has been made clear that the aldose reductase takes part in the crisis of diabetic complication (J. H. Kinoshita et al, J. Am. Med. Assoc. 246, 257 (1981)). Thus inhibition of the aldose reductase may bring prevention and therapy of diseases occurring as diabetic complications.

Compounds possessing blood sugar-lowering action and compounds possessing inhibitory action of aldose reductase have been extensively searched each separately, and, with regard to particular thiazolidine-2,4-dione derivatives, compounds having aldose reductase-inhibitory action or blood sugar-lowering action are known.

For example, as the aldose reductase-inhibitory agents, particular thiazolidine-2,4-dione derivatives are already publicly known (Japanese Unexamined Patent Publication No. Sho 57-28073, Chem. Pharm. Bull. 30(10), 3601, (1982)). Namely, it is publicly known that 5-phenylthiazolidine-2,4-dione derivatives represented by a general formula

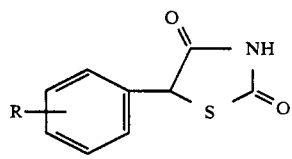

[wherein R denotes a hydrogen atom, lower alkyl group, hydroxyl group, alkoxy group, nitro group, amino group, lower acylamino group, halogen or trifluoromethyl group], have aldose reductase-inhibitory action.

However, thiazolidine-2,4-dione derivatives of the present invention represented by a general formula (1)

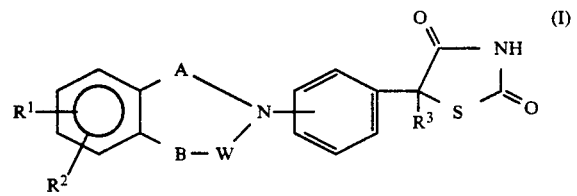

[wherein $R^1$ and $R^2$ each independently represent hydrogen atoms, halogens, lower alkyl groups, hydroxyl groups, lower alkoxy groups, nitro groups or amino groups (said amino group may be substituted with lower alkyl group or lower alkanoyl group), $R^3$ denotes a hydrogen atom or lower alkyl group, A denotes a lower alkylene or carbonyl group, and B and W denote differently lower alkylenes, carbonyl groups or bonding hands], were not known at all, and also it could not be anticipated that thiazolidine-2,4-dione derivatives of the present invention had superior blood sugar-lowering action together with strong aldose reductase-inhibitory action.

The purpose of the present invention is to provide compounds having superior blood sugar-lowering action and simultaneously strong aldose reductase-inhibitory action and being useful as effective and highly-safe drugs capable of preventing and treating diabetes and complication thereof.

DISCLOSURE OF THE INVENTION

As a result of diligent studies for solving such problems, the inventors have found that thiazolidine-2,4-dione derivatives represented by the general formula (1)

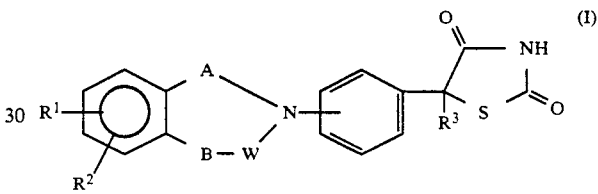

[wherein $R^1$ and $R^2$ each identically represent hydrogen atoms, halogens, lower alkyl groups, hydroxyl groups, lower alkoxy groups, nitro groups or amino groups (said amino group may be substituted with lower alkyl group or lower alkanoyl group), $R^3$ denotes a hydrogen atom or lower alkyl group, A denotes a lower alkylene or carbonyl group, and B and W denote differently lower alkylenes, carbonyl groups or bonding hands], or their salts have superior blood sugar-lowering action and aldose reductase-inhibitory action in combination, leading to the completion of the invention.

For the "lower alkyl" shown in the present invention, straight chain or branched ones with carbon atoms of 1 to 6 such as methyl, ethyl, n-propyl and i-propyl are exemplified. For "halogen", fluorine, chlorine, bromine and iodine are exemplified. For "lower alkoxy", straight chain or branched ones with carbon atoms of 1 to 6 such as methoxy, ethoxy, n-propoxy and i-propoxy are exemplified. For "lower alkanoyl", ones with carbon atoms of 1 to 4 such as acetyl and propionyl are exemplified. "Lower alkylene" means ones with carbon atoms of 1 to 3 and methylene, ethylene, trimethylene, etc. are exemplified. The "eliminating group" is halogen, lower alkoxy or hydroxy and preferable one is halogen. "Their salts" mean salts admissible as drugs and, for example, salts with cations such as sodium and potassium or with inorganic acids (hydrochloric acid, sulfuric acid, etc.) or organic acids (p-toluenesulfonic acid etc.) can be included. (1) Compounds represented by the general formula (1) can be obtained by reacting compounds represented by a general formula (2)

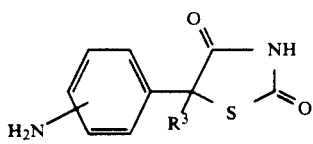

(2)

[wherein $R^3$ is same as above], with compounds represented by a general formula (3)

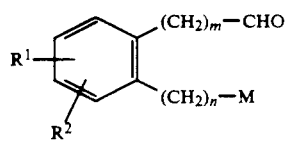

(3)

[wherein m and n indicate integers of 0 to 2, M denotes carboxyl group or its reactive derivative, and $R^1$ and $R^2$ are same as above], in a solvent inert to reaction such as ethanol in the presence of reducing agent such as sodium borohydride, for example, to obtain compounds represented by a general formula (4)

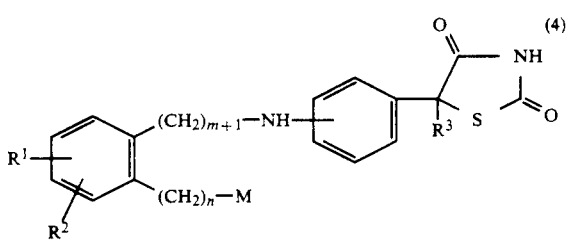

(4)

[wherein $R^1$, $R^2$, $R^3$, m, n and M are same as above], and then by cyclizing. The cyclization can be conducted in the presence of base or acid. As the bases, alkali metal alkoxide such as sodium methoxide, for example, and alkali metal hydride such as sodium hydride, for example, are exemplified, and the reaction is carried out within a temperature range from room temperature to boiling point of solvent. The acids are organic acids such as acetic acid and p-toluenesulfonic acid, for example, and inorganic acids such as hydrochloric acid and hydrobromic acid, for example, and the reaction is conducted usually under heat using excess quantity of acid. In both cases, reaction is conducted in a solvent inert to reaction such as methanol, ethanol or dimethylformamide.

(2) Compounds of the general formula (1) can be obtained by reacting compounds represented by the general formula (2) with compounds represented by a general formula (5)

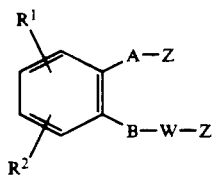

(5)

[wherein Z denotes an eliminating group, and $R^1$, $R^2$, A, B and W are same as above], in the presence of suitable base. This reaction can be conducted beneficially in a solvent such as dioxane, dimethylformamide or ethyl acetate in the presence of alkali metal hydride such as sodium hydride, for example, alkali metal hydroxide such as sodium hydroxide, for example, alkali metal carbonate such as potassium carbonate, for example, or organic base such as pyridine or triethylamine, for example, as a base. The reaction temperature is within a range of 40° to 120° C. and the reaction completes for 1 to 5 hours.

(3) Moreover, compounds of the general formula (1) are obtained by reacting compounds represented by the general formula (2) with compounds represented by a general formula (6)

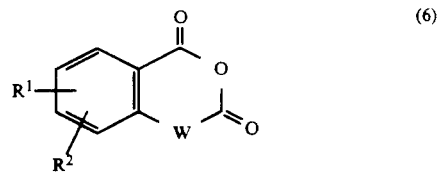

(6)

[wherein $R^1$, $R^2$ and W are the same as above]. in a solvent inert to reaction such as dioxane to obtain compounds represented by a general formula (7)

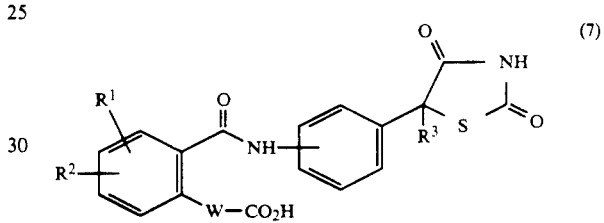

(7)

[wherein $R^1$, $R^2$ and W are same as above], or compounds represented by a general formula (8)

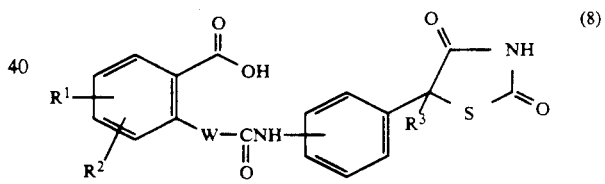

(8)

[wherein $R^1$, $R^2$, $R^3$ and W are same as above], and then by cyclizing. The cyclization is conducted usually under heat using excess quantity of acetic acid. Also, the addition of base such as doium acetate is beneficial. The compounds obtainable through said processes can be isolated. and purified by publicly known separation and purification means, for example, solvent extraction, recrystallization, chromatography, etc. If pharmaceutically admissible salts of compounds represented by the general formula (1) are further needed, they can be obtained by reacting with cation-copossessing bases such as sodium hydroxide and potassium hydroxide, for example, inorganic acids such as hydrochloric acid and sulfuric acid, for example, and organic acids such as fumaric acid and oxalic acid, for example.

BEST EMBODIMENT TO PUT THE INVENTION INTO PRACTICE

The preparative examples and examples of the inventive compounds will be described to illustrate the invention in more detail.

EXAMPLE 1

5-(4-(1-Oxoisoindoline-2-yl)Phenyl)Thiazolidine-2,4-Dione

Into 50 ml of ethanol were dissolved 4.90 g of 5-(4-aminophenyl)-thiazolidine-2,4-dione and 3.54 g of phthalaldehydic acid, and the solution was refluxed for 2 hours. After cooling by standing, 1.78 g of sodium borohydride were added and the mixture was stirred for 20 minutes at room temperature. Thereafter, solvent was distilled off under reduced pressure and 10 ml of glacial acetic acid were added to the residue, which was stirred for 10 minutes at 100° C. After cooling by standing, 100 ml of water were added and the crystals deposited were collected by filtration, washed with water and dried. These were recrystallized from ethanol to obtain 6.90 g of title compound.

m p 257.0°–259.0° C.
Elemental analysis (%) As $C_{17}H_{12}N_2O_3 S$
Calculated: C; 62.95; H; 3.73; N; 8.64.
Observed: C; 63.11; H; 3.72; N; 8.59.

EXAMPLE 2

By the similar method to Example 1, following compound was obtained.

5-(4-(5-Chloro-1-Oxoisoindoline-2-yl)Phenyl)-Thiazolidine-2,4-Dione m.p. >300° C.
Elemental analysis (%) As $C_{17}H_{11}Cl_{1}N_2 O_3 S$
Calculated: C;56.91; H;3.09 N; 7.81.
Observed: C; 57.21; H; 2.99; N; 7.75.

EXAMPLE 3

5-(4-(1,3-Dioxoisoindoline-2-yl)Phenyl)Thiazolidine-2,4-Dione

Into 30 ml of dioxane were dissolved 1,00 g of 5-(4-amino-phenyl)thiazolidine-2,4-dione and 0.74 g of phthalic anhydride, and the solution was refluxed for 2 hours. Thereafter, 30 ml of acetic acid and 0.5 g of sodium acetate were added and the mixture was refluxed for 2 hours. The reaction liquor was poured into 400 ml of water, and the crystals deposited were collected by filtration. These were recrystalized from ethanol to obtain 1.50 g of title compound.

m.p. 243.0°–245.0° C.
Elemental analysis (%) As $C_{17}H_{10}N_2 O_4 S$
Calculated: C; 60.35; H; 2.98; N; 8.28.
Observed: C; 60.44; H; 2.78; N; 8.21.

EXPERIMENT 1

Enhancement of Insulin Sensitivity in Rats

After rats were orally administered with the compound of Example 1 once daily for 5 days at 10 mg/kg/day, they were fasted for 18 hours and then insulin was intraperitoneally injected at 0.1 unit/kg. Blood samples were collected from the tail vein 0 and 1 hour after the injection of insulin for the determination of blood glucose (Table 1).

EXPERIMENT 2

Improvement of Glucose Tolerance in Genetically Obese Mice

Genetically obese mice (CS57BL ob/ob mice) were orally administered with the compound of Example 1 once daily for 5 days at 10, 30 or 100 mg/kg/day, respectively. They were fasted for 18 hours and then 2 g/kg of glucose was orally administered. Blood samples were collected from the tail vein 0, 30, 60 and 120 minutes after the administration of glucose for the determination of blood glucose (Table 2).

From these results in Tables 1 and 2, it was shown that the compound of the present invention possessed potent blood glucose lowering action.

EXPERIMENT 3

Inhibition of Aldose Reductase in Vitro

According to the method of Hyman and Kinoshita (J. Biol. Chem., 240, 877, 1965), inhibitory activity of the compound of Example 23 on aldose reductase extracted from rat lens was investigated. As a result, the following $IC_{50}$ value was obtained (Table 3).

From these result in Table 3, it was suggested that the compound of the present invention possessed potent inhibitory activity on aldose reductase.

TABLE 1

| Group | n | 0 hour value–1 hour value (mg %) |
|---|---|---|
| Reference (insulin only) | 5 | 11.0 ± 0.8 |
| Example 1 10 mg/kg | 5 | 23.0 ± 1.2* |

*$P < 0.01$

TABLE 2

| Compound | OGTT (% of control) | | |
|---|---|---|---|
| | 10 mg/kg | 30 mg/kg | 100 mg/kg |
| Example 1 | 98.2 | 84.1 | 81.1 |

TABLE 3

| Compound | $IC_{50}$ value |
|---|---|
| Example 1 | $9 \times 10^{-8}$ M |

UTILIZABILITY IN THE INDUSTRY

The novel thiazolidine-2,4-dione derivatives and their salts in accordance with the invention possess superior blood sugar-lowering action together with remarkable aldose reductase-inhibitory action, thus they are useful as the drugs for the therapy and prevention of diabetes and the complication thereof:

We claim:

1. Thiazolidine-2,4-dione derivatives represented by a general formula (1)

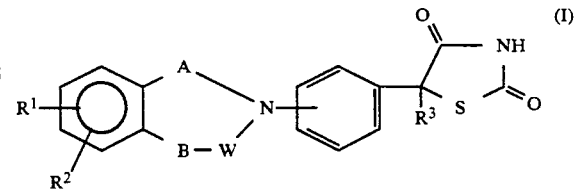

wherein $R^1$ and $R^2$ each identically represent hydrogen atoms, halogens, lower alkyl groups, hydroxyl groups, lower alkoxy groups, nitro groups or amino groups wherein said amino group may be substituted with lower alkyl group or lower alkanoyl group, $R^3$ denotes a hydrogen atom or lower alkyl group, A denotes a lower alkylene or carbonyl group, and B and W denote differently lower alkylenes, carbonyl groups or a bond, or their salts.

2. A blood sugar-lowering agent as in claim 1 having at least one kind of thiazolidine-2,4- dione derivatives represented by the general formula (1)

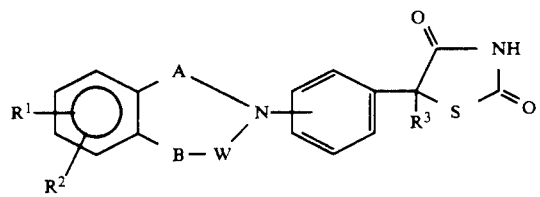

wherein $R^1$, $R^2$, $R^3$, A, B and W are as defined in claim 1, or their salts as effective ingredient(s).

3. An aldose reductase-inhibitory agent as in claim 1 having at least one kind of thiazolidine-2,4-dione derivatives represented by the general formula (1)

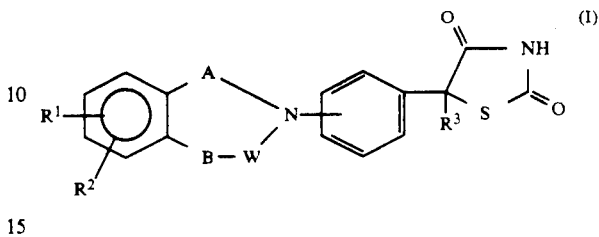

wherein $R^1$, $R^2$, $R^3$, A, B and W are as defined in claim 1, or their salts as effective ingredient(s).

* * * * *